United States Patent
Andersen et al.

(10) Patent No.: US 10,709,816 B2
(45) Date of Patent: Jul. 14, 2020

(54) IMPLANT

(75) Inventors: Olaf Andersen, Dresden (DE); Ingrid Morgenthal, Dresden (DE); Thomas Studnitzky, Dresden (DE); Frank Witte, Hannover (DE)

(73) Assignees: Medizinische Hochschule Hannover (MHH), Hannover (DE); Fraunhofer-Gesekkschaft zur Foerderung der angewandten Forschung e.V., Munich (DE)

( * ) Notice: Subject to any disclaimer, the term of this patent is extended or adjusted under 35 U.S.C. 154(b) by 78 days.

(21) Appl. No.: 14/234,681

(22) PCT Filed: Jul. 27, 2011

(86) PCT No.: PCT/DE2011/001539
§ 371 (c)(1),
(2), (4) Date: May 7, 2014

(87) PCT Pub. No.: WO2013/013648
PCT Pub. Date: Jan. 31, 2013

(65) Prior Publication Data
US 2014/0324188 A1    Oct. 30, 2014

(51) Int. Cl.
*A61L 27/58* (2006.01)
*A61F 2/30* (2006.01)
(Continued)

(52) U.S. Cl.
CPC .......... *A61L 27/58* (2013.01); *A61B 17/8085* (2013.01); *A61F 2/02* (2013.01);
(Continued)

(58) Field of Classification Search
CPC ............................ A61B 17/8085; A61L 27/58
See application file for complete search history.

(56) References Cited

U.S. PATENT DOCUMENTS 6,240,616 B1 * 6/2001 Yan ........................... A61F 2/91
29/527.2
6,365,092 B1 * 4/2002 Backa .................. B01D 53/885
264/628

(Continued)

FOREIGN PATENT DOCUMENTS

DE       1000097 B       1/1957
DE       19712625 A1    10/1998
(Continued)

OTHER PUBLICATIONS

O. Andersen: "Aluminiumfaser-Strukturen fur Adsorptions Kaltemachinen", Apr. 6, 2011, pp. 1-2, XP55024408.
(Continued)

*Primary Examiner* — Bruce E Snow
*Assistant Examiner* — Melissa A Hoban
(74) *Attorney, Agent, or Firm* — Smartpat PLC

(57) ABSTRACT

The invention relates to implants that are implanted into living beings as temporary implants and that disintegrate in the body through biological adsorption over a period of time, in addition to a process for producing aforesaid implants. The implant according to the invention consists of magnesium or a magnesium master alloy. It is formed from fibers of magnesium or a magnesium master alloy that are connected to one another through sintering bridges that are locally spaced vis-à-vis each other and form an open-pored body. The fibers may be produced with the help of the melt extraction process and may subsequently be sintered with one another.

14 Claims, 1 Drawing Sheet

(51) Int. Cl.
*A61L 27/04* (2006.01)
*C22C 49/14* (2006.01)
*B22F 1/00* (2006.01)
*A61L 31/14* (2006.01)
*B22F 9/06* (2006.01)
*A61B 17/80* (2006.01)
*A61F 2/28* (2006.01)
*A61F 2/02* (2006.01)
*A61B 17/00* (2006.01)

(52) U.S. Cl.
CPC ............ *A61F 2/28* (2013.01); *A61F 2/30767* (2013.01); *A61L 27/047* (2013.01); *A61L 31/148* (2013.01); *B22F 1/004* (2013.01); *B22F 9/06* (2013.01); *C22C 49/14* (2013.01); *A61B 2017/00004* (2013.01); *A61B 2017/00526* (2013.01); *A61F 2002/30062* (2013.01); *A61F 2002/3092* (2013.01); *A61F 2002/30968* (2013.01); *A61F 2310/00041* (2013.01); *Y10T 29/49* (2015.01)

(56) References Cited

U.S. PATENT DOCUMENTS

| | | | | |
|---|---|---|---|---|
| 6,395,168 | B1* | 5/2002 | Acernese | C02F 1/50 210/198.1 |
| 8,974,541 | B2* | 3/2015 | Nies | A61L 24/02 623/23.6 |
| 2005/0079088 | A1 | 4/2005 | Wirth et al. | |
| 2005/0163821 | A1* | 7/2005 | Sung | A61F 2/88 424/426 |
| 2007/0003753 | A1* | 1/2007 | Asgari | A61L 27/28 428/315.5 |
| 2007/0244569 | A1* | 10/2007 | Weber | A61F 2/07 623/23.75 |
| 2008/0082162 | A1* | 4/2008 | Boismier | A61F 2/91 623/1.38 |
| 2008/0103594 | A1* | 5/2008 | Loffler | A61L 27/427 623/11.11 |
| 2008/0249637 | A1* | 10/2008 | Asgari | A61F 2/28 623/23.72 |
| 2009/0081313 | A1 | 3/2009 | Aghion et al. | |
| 2010/0036429 | A1* | 2/2010 | Buck | A61B 17/8085 606/280 |
| 2011/0082564 | A1* | 4/2011 | Liu | A61F 2/28 623/23.72 |
| 2013/0150978 | A1* | 6/2013 | Nies | A61L 24/02 623/23.6 |
| 2014/0154341 | A1* | 6/2014 | Manuel | A61L 27/047 424/682 |

FOREIGN PATENT DOCUMENTS

| | | |
|---|---|---|
| DE | 10241572 A1 | 3/2004 |
| DE | 102006005510 | 8/2007 |
| DE | 102008046197 B3 | 12/2009 |
| DE | 102008037204 A1 | 2/2010 |
| JP | 2005505685 | 2/2005 |
| JP | 2009-535504 | 10/2009 |
| WO | WO03055537 A2 | 7/2003 |
| WO | WO 2013/013648 A1 | 1/2013 |

OTHER PUBLICATIONS

G. Stephani et al., "New multifunctional lightweight materials based on cellular metals—manufacturing, properties and applications", J. Physics, Series 165, 2009, pp. 1-7.

* cited by examiner

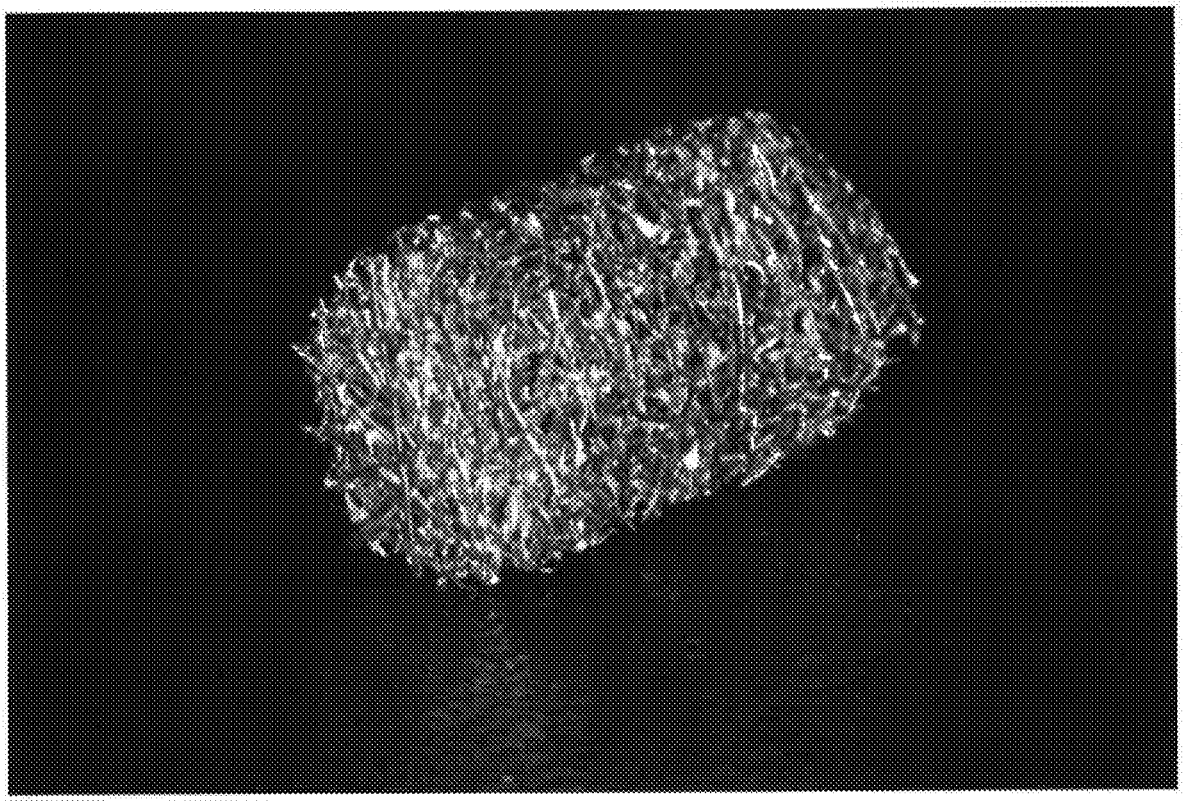

IMPLANT

This is a national stage of PCT/DE11/001539 filed Jul. 27, 2011 and published in German, hereby incorporated by reference.

The invention relates to implants that are implanted as temporary implants into living beings and that disintegrate in the body over time with the help of biological resorption.

In principle, such implants have been known as having been made from a wide range of different materials. DE 10 2008 037 204 A1 describes a plate for the attachment of bone fragments that comprises a pressed form body made from wire. Preferably, this form body should be a pressed knit. Among others, magnesium or a magnesium alloy are mentioned therein as suitable materials for the wires to be thus utilized.

During production, the wires should be folded and/or rolled up as netting and subsequently machined through pressing into a form body.

In doing so, however, the possibility of the geometric structure of such an implant is limited, and particular form and press tools are required, respectively. It is also described how borings may be made. As a rule, in order to do this, a certain placement of the wires into the form tool is necessary, taking into account the arrangement of a boring. Moreover, a corresponding press tool that has been adapted to the desired form of the implant, is required. The inserted wires must have a certain sufficient length in order to achieve a secure connection, which is problematic with magnesium and magnesium master alloy, particularly with respect to the desired changed forming during pressing.

BRIEF DESCRIPTION OF THE DRAWING

The FIGURE shows a photograph of the invention made as described below.

A subsequent forming or, in particular, the production of several implants from a slug is no longer possible.

For certain types of applications, the flexible workableness of such implants is disadvantageous on account of their pliability, since the wires are not firmly attached to each other.

Thus it is the task of the invention to present possibilities with which biologically absorbable implants that can be manufactured flexibly and inexpensively and do not cause physiological concerns regarding the implantation, can be provided.

This task is solved with an implant as disclosed in this specification. It may be manufactured in a process as disclosed in this specification.

The implant in accordance with the invention consists of magnesium or a magnesium master alloy. It is formed from fibers of magnesium or of a magnesium master alloy that are connected with one another through sintered bridges that are locally spaced vis-à-vis each other such that they form an open-pored body.

The fibers should have a length ranging from 2 mm to 15 mm, preferably ranging from 5 mm to 10 mm and/or an outer diameter ranging from 0.05 mm to 0.5 mm. This enables their inexpensive production and easy further machining.

It is advantageous if the magnesium master alloy is made with at least one metal with which a liquid phase may be achieved at a temperature that is below the melting temperature of pure magnesium. This, too, provides the possibility to keep the proportional share of the liquid phase that was formed at less than 20%. Thereby, both a secure connection of the fibers via the sintered bridges at the touching positions and a sufficient strength of the fiber connection may be achieved.

Thus, a magnesium master alloy may contain, in addition to magnesium, at least one metal that is chosen from Y, Zn, Ca, Mn, Pd, Ag, Sr, Bi, Si, Pr, Ga, Sc, Zr, Ce, Eu, La, Nd, Na and Li.

In this context, a magnesium master alloy should be understood to mean an alloy in which the magnesium portion is greater than 50%, and preferably greater than 75%.

The alloy should not contain aluminum, copper or nickel, except for traces of maximally 1%, and preferably maximally 0.1%.

The implant should have a porosity ranging from 50% to 95%. Alone or additionally, it should have a volume-specific surface ranging from 5000 $m^2/m^3$ to 50000 $m^2/m^3$.

It is advantageous if a magnesium oxide layer and/or a fluoride layer is formed on the surface of the fibers, at least in certain areas. This layer should preferably have a layer thickness of at least 0.1 μm. Such an oxide layer or fluoride layer is capable of influencing the speed of degradation with which the implant is adsorbed in a living body so that it will be adsorbed fully and thus without residue after an appropriate, predetermined period of time, therefore making superfluous any surgical removal of the implant. The thicker the aforesaid oxide layer or fluoride layer is, the longer the complete adsorption may be delayed. Moreover, there may be areas on an implant on which a magnesium oxide layer has been formed and other surface areas are provided with a magnesium fluoride layer. Thereby, too, a different period of time may be applicable for the complete degradation of such areas of an implant. To this end, an implant that has been provided in certain portions of its surface with a magnesium oxide layer, may be partially submersed into a fluoride solution and subsequently dried, so that the submersed area thereby is additionally provided with a fluoride layer.

Suitable fluorides are for example magnesium fluoride or sodium fluoride.

In the case of a partial coating, uncoated areas of areas with a lesser oxide layer thickness are adsorbed more quickly than coated areas, thus also enabling a locally targeted influencing.

An implant may also contain areas with different porosity and strength, so that an adjustment to each desired application is made possible. In doing so, the packing density of fibers and thus the porosity in the respective areas may vary. Increased packing density, meaning more fibers per volume unit, may increase the strength in such an area and correspondingly reduce the strength in other areas. The growing-in behavior of tissue thus also can be influenced locally in a targeted manner.

The production of an implant from magnesium or from a magnesium master alloy may involve the production of fibers through a melting extraction process from molten magnesium or a molten magnesium master alloy in an inert atmosphere. In principle, the process of melting extraction is also described a. o. in DE 100 00 97 A1 and DE 10 2006 005 510 A1, in addition to different possible embodiments.

The fibers that were thus produced are deposited in bulk form or as an aggregate, respectively, onto a base or into a form comprised of an inert material; subsequently, sintering is carried out in an inert atmosphere, through which the fibers are connected to one another through sintering bridges that are locally spaced vis-à-vis each other.

When using a magnesium master alloy for the production, sintering may be carried out at a temperature that is lower than the melting temperature of pure magnesium, since the desired liquid melting phase that is required in order to achieve a desirable liquid phase sintering in the area of the sintering bridges to be formed, with a suitably chosen magnesium master alloy, may be achieved with a correspondingly lowered temperature.

The aforementioned magnesium oxide layer on the surface of the fibers may be formed with the help of an anodic oxidation, plasma chemical oxidation or thermal oxidation. This occurs after the sintering process.

The invention enables the production of relatively large format, open-pored bodies with the connected fibers, that also may be semi-finished products that may be divided into several individual implants through the application of suitable cutting processes or separation processes, thereby reducing the production cost and effort. By applying such a process, the external geometry and/or dimensioning of an implant may be adjusted to the relevant requirements. The application of laser beams has shown itself to be a suitable separation process, whereby in this case, too, a protective gas atmosphere (e.g. Ar) should be observed. Even after the separation of parts or areas of the sintered, open-pored body, the latter's strength is preserved, at least for the most part. This applies to both its compressive and tensile strength. Moreover, the compound of the fibers that have been sintered with one another is retained. This shaping should, however, take place prior to a potentially desired formation of a magnesium oxide layer.

In addition to the already mentioned contamination with additional metals, such as aluminum or other alien agents or auxiliary agents (tracers) can be avoided. The implant consists at least almost exclusively of magnesium, the relevant magnesium master alloy and, if applicable, the magnesium oxide layer and/or fluoride layer. Thus, expensive registration procedures can be avoided, since the required biocompatibility proofs have already been provided, and a product permit may be obtained easily and with relatively little input. In particular, no organic components or placeholders are present, as these, in contrast to the production of metal foam, not are necessary for production. No proof is required that organic and other residues are not contained in the final manufactured implant.

In contrast to foaming, a complete, open porosity is possible.

An open-pored body applicable in the invention as an implant according to the invention, may also be applied to another, preferably metallic implant (e.g. a prosthesis) with no or very little porosity and be connected to it, preferably by positive substance jointing. Thereby, the growing in of tissue or bones, in addition to the osseous anchoring may be improved. An implant according to the invention can thus be termed a temporary implant which subsequently is connected to a permanent implant (e.g. the shaft of a hip prosthesis). The fiber mesh that, as a consequence of the degradation process, is of a temporary nature, enables bones to grow in better, whereby a faster and secure anchoring of the hip shaft can be achieved. After the implant according to the invention has disintegrated, the basic form (e.g. the rough surface of the hip shaft) is ultimately in contact with the bone.

Below, the invention will be explained in greater detail with the help of examples.

EXAMPLE 1

Metallic short fibers are produced from an alloy MgY4 (4 mass-% yttrium, rest magnesium) with the help of the melting extraction process. The magnesium master alloy is smelted inductively in an Ni-free steel crucible at a temperature of 680° C. The extraction roller is submersed into the molten bath, the melt moistens the roller, and the rotating roller entrains small amounts of melt that solidify on the cooled roller, detach from the roller surface and are captured in a receptacle. Additional parameters such as crucible lift and rotation speed, in addition to the notch distance of the roller, determine the geometry of the short fibers that are produced, such as fiber length and median fiber diameter/outer diameter/surface diagonal. Due to their solidifying at the edge of the roller surface, the fibers have a typical half-moon or sickle-shaped cross-section, and the rapid solidification leads to the characteristic solidification structure.

In order to prevent the formation of oxide on the fiber surface, the melting extraction facility is flooded with argon protective gas, so that the fibers are extracted in an inert atmosphere.

The evaporation of Mg is problematic on account of the high vapor pressure that is characteristic for the material, thus making the control of the extraction parameters through the view window more difficult. With a variation 2 (Example 2) involving the covering of the melt with loosely resting ferrous hollow spheres, it was clearly possible to reduce the evaporation in the area of the extraction facility.

Table 1 contains the most important data of the melting extraction of different MgY4 fiber charges, and Table 2 contains the characteristic fiber values.

In Example 1, MgY4 fibers that have a median circle-equivalent diameter of 216±68 μm and a median fiber length of 7.2 mm are produced without a melt bath cover. These fibers are characterized by a high degree of purity, comparable to that of the parent material (melt ingot). In the overall analysis, oxygen is determined to be ≤0.002%.

In order to obtain a highly porous, open-cell sintering body from Mg short fibers, prior to the actual sintering process, a defined bulk volume of fibers is produced. This is carried out with the help of a sieve (sieve drum for large charges). The fibers are scattered evenly, layer by layer, onto a sintering substrate. Subsequently, the fibers are sintered in the furnace by applying parameters that enable the achievement of a highly porous and at the same time, firm sintering bond. Sintering takes place at a temperature that is lower than the melting temperature of the magnesium master alloy, at a temperature ranging from 625° C. to 630° C., at which temporary liquid phases are formed. A liquid phase portion ranging from 10% to 20% in the area of the sintering temperature is advantageous for the achievement of a stable sintering bond and is a precondition for the sintering of materials with surface oxide formation, as is the case with Mg.

The fibers should not react with the sintering substrate, which, at the same time means, that the sintered sample should be easily detachable from the sintering substrate. For this reason, the MgY4 fibers were deposited onto an inert substrate made from sheet tantalum such that the structure will show the desired porosity of 75% after sintering has taken place. The tantalum substrate and cover plate ensure that the chemical composition of the fibers will not change during sintering.

A bulk volume was produced with the required spatial extensions so that the dimensions 100 mm*50 mm*3 mm can be achieved in the desired porosity.

The sintering took place in the protective gas furnace (silica glass pipe) under high-purity argon 6.0 by heating the charge with 10 K/min to 600° C., at a holding time of 1 min and subsequent additional heating with 3 K/min to a sintering temperature $T_{max}$ of 628° C. In order to prevent oxygen from the furnace atmosphere from intruding into the fibers, titanium was used as gettering material.

The sintered structure is characterized by stable sinter contacts in the area of the sintering bridges, high median porosity of 73.5% and very good machinability. The machining into defined, open-pored form bodies may take place through sawing (dry) or laser cutting. Open-pored bodies with defined geometry such as circles with a 10 mm diameter were produced with the help of laser cutting under argon protective gas.

In order to assess the degradation, corrosion tests were carried out over a period of up to 7 days and at a temperature of 37° C., using Dulbecco's Modified Eagle Medium (DMEM), supplied by Messrs. Biochrom GmbH Berlin. The development of hydrogen (volume V in ml) was used as the measure for the corrosion. Comparative tests of compact material from the MgY4 alloy showed that the degradation of open-pored bodies, when viewed absolutely, leads to a higher release of hydrogen. When, however, taking into account the large surface of the porous bodies and relating the hydrogen volume to the sample surface ($V_N$ in ml/cm$^2$), these perform better than the compact material.

EXAMPLE 2

An open-pored body that was sintered according to Example 1 was superficially oxidized after sintering, through exposure to oxygen at a temperature lower than the sintering temperature. Since the oxidation occurs after sintering, the oxide layer that was formed does not damage the sintering bridges between the fibers. The corrosion test in DMEM shows for this sample an improved durability, i.e. a slowed-down degradation of the fiber bond.

EXAMPLE 3

Analogous to Example 1, MgY4 fibers were produced. For the melt extraction, however, a melt bath cover was applied by arranging ferrous hollow spheres loosely, yet covering the surface, upon the metal to be melted. After the inductive melting of the MgY alloy, the hollow spheres floated upon the melt bath without dissolving in the latter. Thereby, they significantly reduced the evaporation of the melt within the extraction facility.

The fibers that were produced in this manner from MgY4 have a median circle-equivalent diameter of 187±63 m and a median fiber length of 5.8 mm. These fibers are also characterized by a high degree of purity. The chemical analysis of the fibers, as compared to the melt ingot MgY4, did not show any significant changes in the content of Y and no increase in the undesirable elements Al, Cu or Fe. The latter are contained in the parent material in concentrations of <0.004 and/or 0.005%, respectively.

EXAMPLE 4

Analogous to Example 1, fibers of the magnesium master alloy MgY4 were bulked into a highly porous structure and sintered. In contrast to Example 1, the fibers were sintered on a substrate of sheet tantalum that had been coated with an MgO suspension. Prior to the first application, the suspension, consisting of powdered Magnesia 298, dispersed in ethanol, is burned out at 800° C. under argon protective gas. Thereby, a high-purity coating is achieved. The advantageous aspect of this MgO coating is that the open-pored body that was formed with the sintered fibers, can easily be detached after sintering. The subsequent handling is made significantly easier. A possible "anchoring" of the fine MgO particles to the outer fiber zone of the open-pored body that may have occurred due to the sintering process, impacts advantageously upon the corrosion behavior. A slight decrease in corrosion rate was discovered so that the degradation should occur over a longer period of time.

EXAMPLE 5

Analogous to Example 1, fibers of the magnesium master alloy MgY4 were bulked into a highly porous structure and sintered. The sintered, open-pored body is subjected to plasma chemical oxidation. An oxide layer is formed at the surface of the fiber structure. This leads to a significantly slower corrosion in the DMEM (for implementation see Example 1).

TABLE 1

Extraction conditions; fibers MgY4 (3 examples)

| fiber charge | temperature [° C.] | Crucible lift [µm/s] | roller speed [m/s] | test period [min] | Melt bath cover |
|---|---|---|---|---|---|
| (1) D114 | 680 | 20.0 | 3.0 | 10 | none |
| (2) V621 | 800 | 20.0 | 5 | 30 | Hollow spheres |
| (3) V622 | 800 | 20.0 | 4.2 | 30 | Hollow spheres |

TABLE 2

Fiber values from image analysis (*) and scanner analysis (**)

| Fiber charge | Material | density [g/cm$^3$] | median density [µm] () | median length [mm] () | mass-specific surface $A_m$ [m$^2$/g] (*) | equivalent circle diameter [µm] (*) |
|---|---|---|---|---|---|---|
| (1) D 114 | MgY | 1.78 | 224 | 7.2 ± 1.5 | 0.01175 | 216 ± 68 |
| (2) V 621 | MgY4 | 1.78 | 243 | 5.8 ± 1.4 | 0.01349 | 187 ± 63 |
| (3) V 622 | MgY4 | 1.78 | 179 | 5.4 ± 1.7 | 0.01334 | 166 ± 47 |

EXAMPLE 6

The master alloy MgY4 (4 mass-% Yttrium) was molten by adding high-purity Ca granulate in a high-vacuum melting and casting facility into an MgYCa alloy. In order to achieve a thorough mixing of the component parts, they were recast several times.

The finished melting ingot was analyzed in order to determine respective element contents and potential impurities. The analyses showed median values of 2.6% for yttrium and 1.6% for calcium. For the undesirable accompanying elements Cu und Fe, contents of <0.004 and <0.003%, respectively, were determined. Oxygen content was maximally 0.01%.

Analogous to Example 3, fibers are produced from this alloy MgY2,6Ca1,6. This means that the fiber production took place with a melt bath cover through ferrous hollow spheres that are arranged upon the melt bath and during the melt extraction.

The fibers that were thus produced from MgY2,6Ca1,6 (Charge V620) have a median circle-equivalent diameter of 166±75 µm and a median fiber length of 7.4 mm. These fibers, too, are characterized by a high degree of purity. The chemical analysis of the fibers, as compared to the melt ingot MgY4, did not show any significant changes in the Y content and no significant increase in the undesirable elements Cu or Fe. Cu was determined to be 0.004% and Fe was determined to be 0.007%.

The data for the fibers may be seen from Tables 3 and 4.

TABLE 3

Extraction conditions fibers MgY2,6Ca1,6

| fiber charge | temperature [° C.] | Crucible lift [µm/s] | Roller speed [m/s] | Test period [min] | Melt bath cover |
|---|---|---|---|---|---|
| V620 | 800 | 20.0 | 3.5 | 30 | Hollow spheres |

TABLE 4

Fiber values from an image analysis (*) and a scanner analysis (**)

| Fiber charge | Material | density [g/cm$^3$] | Median thickness [µm] () | Median length [mm] () | Mass-specific surface $A_m$ [m$^2$/g] (*) | Equivalent circle diameter [µm] (*) |
|---|---|---|---|---|---|---|
| V 620 | MgY2,6Ca1,6 | 1.74 | 296 | 7.4 ± 1.3 | 0.01531 | 166 ± 75 |

EXAMPLE 7

Fibers that were produced analogously to Example 6, are bulked analogously to Example 1 into a highly porous structure and sintered. Taking into account the ternary phase diagram and thermodynamic calculations for the estimation of sintering temperatures with the help of the PANDAT software, the sintering temperature for the MgY2,6Ca1,6 alloy ranges from 550° C. to 590° C., corresponding to a liquid phase share ranging from 10 to 20%.

A sintering of the fibers from MgY2,6Ca1,6, bulked onto an inert substrate of sheet tantalum was carried out at 580° C. As described in Example 1, the sintering took place in the protective gas furnace (silica glass pipe) under high-purity argon 6.0, by heating the sample with 10 K/min to 550° C., holding time 1 min, and subsequent heating with 3 K/min to the sintering temperature $T_{max}$ of 580° C., holding time 20 min.

The sintered structure is characterized by stable sinter contacts, high porosity of 61% in the test material and very good machinability. The machining into defined form bodies in the form of circles with a diameter of 10 mm was done with the help of laser cutting. The sintered structure is characterized by a high degree of purity (oxygen content max. 0.001%). On account of the changed composition (2.6% Y; 1.6% Ca) the speed of degradation that can be measured in the corrosion test is somewhat greater than is the case with the implant manufactured in accordance with Example 1.

The implants that are manufactured in accordance with the Examples 1 through 7 may be cleaned as follows and subsequently coated. For purposes of cleaning, 20 ml glycerol (85%), 5 ml nitric acid (65%), 5 ml acetic acid (100%) are mixed, and the sintered implant is submersed in the solution for 30 seconds. Subsequently, it is cleansed twice for 60 seconds each time, in 100% ethanol in an ultrasound bath and finally it is blown with a compressed gas cleaner. Thereafter, a complete drying process takes place in the vacuum cabinet at a temperature of 50° C. over a period of approximately 10 minutes.

The implant that was cleaned and dried as described above, may be submersed into a saturated sodium fluoride solution. 4 g in 100 ml aqua ad iniectabilia (Messrs. Baun, 100 ml gas flask) are added to the solution, and the mixture is prepared in a glass container wherein it is stirred for a period ranging from 1 h to 2 h.

The pH value is adjusted to 11.5 by adding NaOH. The implant may be placed in the solution that was thus obtained, and a sodium fluoride layer may be formed on the surface. After having been dried in a vacuum cabinet, the sodium fluoride layer may have a median layer thickness of at least 0.1 µm. Through the coating a significant decrease in corrosion rate, as compared to a non-coated fiber structure, could be achieved.

The invention claimed is:

1. Implant useful for bone in-growth consisting exclusively of a sintered bulked volume of packed layers of scattered fibers of a magnesium master alloy containing greater than 50% magnesium and excluding each of aluminium, copper, and nickel except in traces of maximally 1%, wherein the fibers have a length ranging from 2 mm to 15 mm and are securely connected to each other by sintered bridges that are locally spaced vis-à-vis one another and thereby form an open-pored body, which implant disintegrates in a living being through biological adsorption.

2. Implant according to claim 1, characterized in that the magnesium master alloy is formed with at least one metal with which a liquid phase can be achieved at a temperature lower than the melting temperature of pure magnesium.

3. Implant according to claim 1, characterized in that the magnesium master alloy contains at least one metal selected from the group consisting of Y, Zn, Ca, Mn, Pd, Ag, Sr, Bi, Si, Pr, Ga, Sc, Zr, Ce, Eu, La, Nd, Na and Li.

4. Implant according to claim 1, characterized in that the implant has a porosity ranging from 50% to 95%.

5. Implant according to claim 1, characterized in that at least part of the surface of the fibers has a magnesium oxide layer formed thereon.

6. Implant according to claim 5, wherein the magnesium oxide layer has a layer thickness of at least 0.1 µm.

7. Implant according to claim 1, characterized in that at least part of the surface of the fibers has a fluoride layer formed thereon.

8. Implant according to claim 7, wherein the fluoride layer has a layer thickness of at least 0.1 µm.

9. Implant according to claim 1, characterized in that areas with different porosity and strength are present.

10. Implant according to claim 1, characterized in that the implant is connected to another implant.

11. Implant according to claim 1, characterized in that the fibers have a length ranging from 5 mm to 10 mm.

12. Implant according to claim 1, characterized in that the fibers have an outer diameter ranging from 0.05 mm to 0.5 mm.

13. Implant according to claim 1, characterized in that the implant has a volume-specific surface ranging from 5000 $m^2/m^3$ to 50000 $m^2/m^3$.

14. Implant according to claim 1, wherein the fibers have a half-moon or sickle-shaped cross section.

\* \* \* \* \*